(12) United States Patent
Hagege

(10) Patent No.: US 9,320,893 B2
(45) Date of Patent: Apr. 26, 2016

(54) VAGINAL REHABILITATIVE DEVICE

(71) Applicant: Obensen Ltd., Tortola (VG)

(72) Inventor: Edward Hagege, Herzelya Pituach (IL)

(73) Assignee: Blue Medical Innovation Ltd., Fotan (HK)

( * ) Notice: Subject to any disclaimer, the term of this patent is extended or adjusted under 35 U.S.C. 154(b) by 0 days.

(21) Appl. No.: 13/862,555

(22) Filed: Apr. 15, 2013

(65) Prior Publication Data

US 2013/0274823 A1    Oct. 17, 2013

Related U.S. Application Data

(63) Continuation-in-part of application No. 13/063,949, filed on May 6, 2011, now Pat. No. 8,634,920.

(51) Int. Cl.
*A61N 1/00* (2006.01)
*A61N 1/36* (2006.01)
*A61N 1/05* (2006.01)

(52) U.S. Cl.
CPC .......... *A61N 1/36007* (2013.01); *A61N 1/0524* (2013.01)

(58) Field of Classification Search
CPC .............. A61N 1/0521; A61N 1/0524; A61N 1/36007; A61N 1/36107
USPC ............................................. 607/39–41, 138
See application file for complete search history.

(56) References Cited

U.S. PATENT DOCUMENTS

| | | | |
|---|---|---|---|
| 4,205,671 A | 6/1980 | Lassen | |
| 4,515,167 A * | 5/1985 | Hochman | 600/549 |
| 4,909,263 A * | 3/1990 | Norris | 607/39 |
| 5,702,428 A | 12/1997 | Tippey | |
| 6,086,549 A * | 7/2000 | Neese et al. | 600/587 |
| 7,577,476 B2 | 8/2009 | Hochman et al. | |
| 7,957,794 B2 | 6/2011 | Hochman et al. | |
| 2006/0190049 A1 * | 8/2006 | Gerber et al. | 607/41 |
| 2007/0066995 A1 | 3/2007 | Strother | |
| 2007/0260288 A1 | 11/2007 | Gross | |

FOREIGN PATENT DOCUMENTS

| | | |
|---|---|---|
| GB | 2435834 A | 9/2007 |
| WO | 0160446 A1 | 8/2001 |
| WO | 2007059989 A2 | 5/2007 |

OTHER PUBLICATIONS www.athenaft.com (website pertaining to the Athena pelvic exerciser)—available prior to May 6, 2011.

* cited by examiner

*Primary Examiner* — Scott Getzow
(74) *Attorney, Agent, or Firm* — Roach Brown McCarthy & Gruber, P.C.; Kevin D. McCarthy

(57) ABSTRACT

A vaginal rehabilitative device comprising: a vaginal electrical stimulation applicator; and a control module connectable by a wire to said applicator and comprising a user interface for controlling electrical stimuli by said applicator and a display module configured to display data received from said applicator.

15 Claims, 8 Drawing Sheets

VAGINAL REHABILITATIVE DEVICE

CROSS REFERENCE TO RELATED APPLICATIONS

This application is a Continuation-in-Part of U.S. patent application Ser. No. 13/063,949, filed May 6, 2011, entitled "Device for Perineum Reeducation", which is incorporated herein by reference in its entirety.

FIELD OF THE INVENTION

The invention relates to the field of vaginal rehabilitation devices.

BACKGROUND

Urinary incontinence is often divided to two main types: stress incontinence and urge incontinence. Stress incontinence corresponds to loss of urine as a result of an increase in abdominal pressure on the bladder. This increase in pressure may be caused due to coughing, sneezing, laughing, or making a movement, in particular lifting a heavy object. Stress incontinence is the most common type of incontinence and it mainly affects women. It takes place in general when the perineal muscles and the muscles of the floor of the pelvis are weakened, e.g. by pregnancies, childbirth, or menopause.

Urge incontinence corresponds to a sudden need to urinate, followed by an immediate contraction of the bladder. This contraction results in an involuntary loss of urine. Both men and women may be affected by this type of incontinence, in particular among older people. One of the reasons for such incontinence is a failure in the operation of the nervous system controlling the bladder.

Mixed incontinence is a combination of stress incontinence and of urge incontinence.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with some embodiments, a perineal rehabilitation device comprising: an electrical stimulation applicator; and a control module connectable by a wire to said applicator, and configured to control said applicator, the control module comprising a user interface for controlling said applicator and a display module configured to display data received from said applicator.

In some embodiments, said applicator is shaped as an elongated rounded cylinder, for endocavity use.

In some embodiments, said applicator is shaped as an annular band, for external use.

In some embodiments, said applicator further comprises at least one energy storage unit.

In some embodiments, said applicator further comprises at least one microprocessor, configured to manage said applicator operation.

In some embodiments, said applicator further comprises at least two stimulation electrodes, configured to apply voltage for executing electrical stimulation.

In some embodiments, said applicator further comprises at least two charging electrodes, configured to be connected to power source while said applicator is charging.

In some embodiments, said applicator further comprises a dedicated electrode configured to detect if said applicator is positioned correctly to allow stimulation activation.

In some embodiments, said applicator further comprises a sensor configured to detect body reaction to electrical stimulation, for allowing adaptive stimulation and feedback of treatment effectiveness.

In some embodiments, said sensor is a pressure sensor, configured to sense muscle contraction.

In some embodiments, said control module further comprises at least one energy storage unit.

In some embodiments, said control module further comprises at least one microprocessor, configured to manage said control module operation.

In some embodiments, said control module further comprises a memory for storing data regarding the treatment history.

In some embodiments, said applicator and said control module are configured to communicate via bidirectional wired communication protocol.

In some embodiments, said control module is further configured to communicate with a computer via wired communication protocol, for further viewing and analyzing.

In some embodiments, said control module is further configured to communicate with a computer via wireless communication protocol, for further viewing and analyzing.

There is further provided, in accordance with some embodiments, a method for perineal rehabilitation comprising: selecting desired stimulation program using a control module; selecting desired treatment duration using said control panel; applying stimulation applicator to suitable body part and waiting for confirmation of correct applying on said control module; performing sensitivity test to define user sensitivity threshold; running the selected stimulation program; receiving feedback from user body by a sensor installed in said applicator; adjusting stimulation parameters while said program is running, if needed; extracting said applicator after treatment end; viewing data on said control module; and optionally connecting said control module to a computer, for viewing data stored on said control module.

In some embodiments, said program is selected from multiple programs, pre-determined and dedicated for treatment of different medical diagnosis, programmed in said control module.

In some embodiments, said sensitivity test is done by applying stimulation at zero intensity level and increasing stimulation manually by user, stopping the stimulation by the user when it is initially felt, and storing the corresponding intensity level on said control module memory.

In some embodiments, said sensitivity test is done by applying stimulation at zero intensity level and increasing stimulation automatically by said control module, stopping the stimulation by the user when it is initially felt, and storing the corresponding intensity level on said control module memory.

In some embodiments, said selected stimulation program parameters are displayed to the user on said control module, while said program is running.

In some embodiments, said selected stimulation program parameters can be changed and said program can be stopped by the user at any time, while said program is running.

In some embodiments, said selected stimulation program can be stopped automatically at any time if the applicator misplaced from its correct location on suitable body part, while said program is running.

In some embodiments, said receiving feedback from user body is done by measuring muscle contraction, and used for adaptive stimulation.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Disclosed herein are a device and a method for vaginal rehabilitation. The present device, according to some embodiments, may be a mobile, liquid-sealed, easy to use electrical stimulator for treating one or more conditions such as urine incontinence, organ prolapsed and/or the like.

Figure 1B:
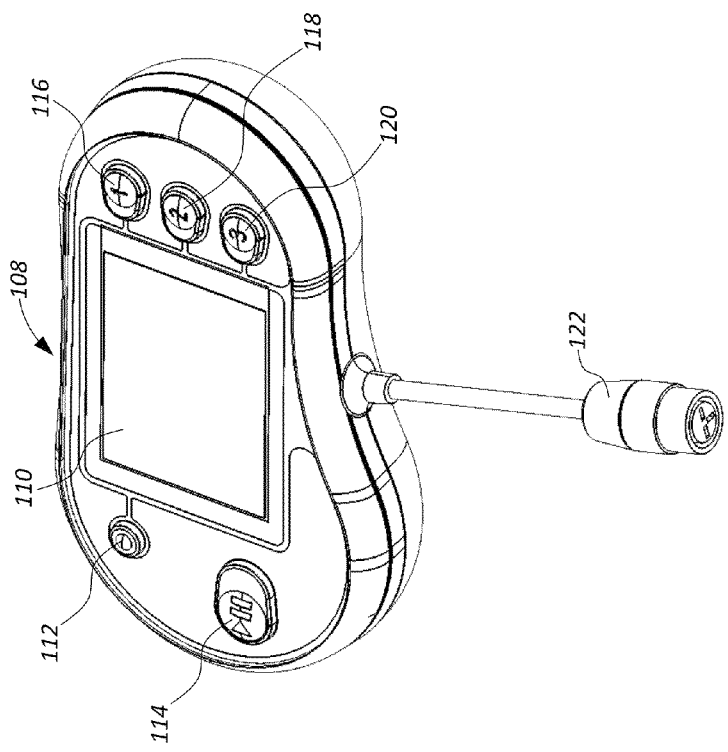
FIG. 1B shows an illustration of a control module of a rehabilitation device, in accordance with some embodiments.
Figure 1A:
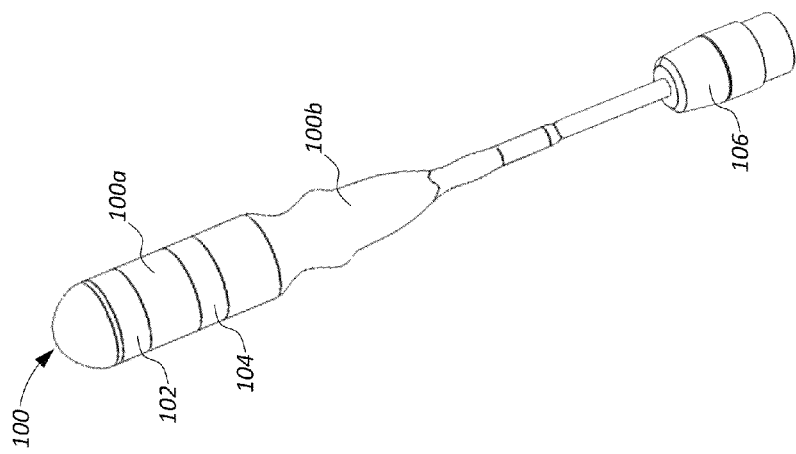
FIG. 1A shows an illustration of an endocavity applicator of a rehabilitation device, in accordance with some embodiments.
Figure 1C:
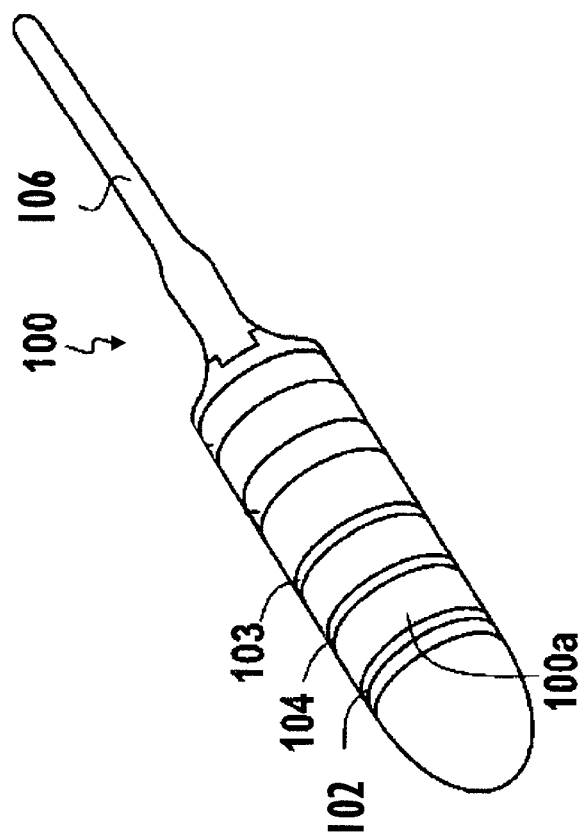
FIG. 1C shows an illustration of an endocavity applicator with a detection electrode, in accordance with some embodiments.

Present embodiments may be better understood with reference to the accompanying drawings. Reference is now made to FIG. 1, which shows an illustration of a perineal rehabilitation device. Depicted is an endocavity applicator 100 which may comprise an oblong portion 100a for inserting into the cavity (e.g. the vagina), and a long thin portion 100b which may comprise a handle for inserting and removing the applicator. The endocavity applicator may be sealed so as to be easy to clean. Oblong portion 100a may be equipped with multiple annular stimulation electrodes, by way of example herein two electrodes 101 and 102. Other electrode shapes, in particular circular arcs may also be implemented. Stimulation electrodes 101 and 102 may be used to apply the electrical stimuli. The number of stimulation electrodes may be greater. Nevertheless, studies have shown that the ratio of the number of electrodes to the effectiveness of stimuli is very satisfactory when using two electrodes. Assuming the device may be designed for vaginal use in such manner that oblong portion 100a is inserted in full, stimulation electrodes 101 and 102 may occupy the first four centimeters of oblong portion 100a, since it may be their optimal and most effective location.

Applicator 100 may include at least one microprocessor for managing the stimuli, and a communication module, for wire communicating with a control module 108. Control module 108 may function as a remote control for the user. Control module 108 may include a display screen 110 and multiple control buttons, by way of example herein five buttons 112, 114, 116, 118, 120. Control module 108 may also include a battery, at least one microprocessor, at least one memory module for storing data, and a communication module for wire communicating with applicator 100. Button 112 may serve to switch the device on and off. Button 112 may be also used for stopping the stimulation at any moment. Button 114 may enable the treatment to be started and paused momentarily. Buttons 116, 118 and 120 may serve as multi-functional keys, allowing controlling a variety of changing functionalities, such as validation of choices, selecting treatment, setting treatment duration and intensity, view session report, setting preferred language, date and time, etc. Applicator 100 and control module 108 may apply wired communication between them. Any type of wired communication protocol may be used, such as Ethernet, USB (Universal Serial Bus), etc. wired communication may be obtained via applicator connector 106 and control module connector 122, by way of example herein DIN3 connectors, which may be connected with a wire suitable for the communication protocol of choice. Specifically, muscular contraction may weaken after several successive contractions. It may then become inefficient for the muscle that is fatigued or that is becoming fatigued to be stimulated strongly. Advantageously, applicator 100 may include a sensor for measuring the reactions of the user's body, e.g. a pressure sensor suitable for measuring muscle contraction, which may be implemented by a strain gauge. The measurement of this contraction may then be transmitted in real time to control module 108, which may adjust the stimulation intensity according to measured muscle contraction, for creating an adapted use. Moreover, this data may be recorded on control module memory, to provide feedback of user advancement to the user and/or to health professional, in real time during treatment session and/or during report analysis after treatment.

According to an advantageous characteristic of the invention, the applicator 100 includes a third electrode 103 for detecting that it has been inserted or installed in a body cavity, e.g. the vagina, to avoid electric shocks. Electrode 103 is suitable for detecting contact with the body, said electrode being suitable for sending a signal to the microprocessor installed within the applicator and/or the microprocessor installed within the control module, the microprocessor being such as to be suitable for causing stimulation to stop as soon as the applicator is no longer in contact with the body or when the applicator 100 is extracted from the vagina.

In addition to sensor 103, the electric current or intensity can be reduced to zero at any moment so as to allow removing the applicator at any moment. The sensor 103 then serves to verify that the applicator 100 is indeed inserted before beginning the treatment. The signal issued by the sensor 103 is sent to the control module.

According to the invention, it is also advantageous for the software managing the operation of the applicator 100 to stop the stimulation as soon as the sensor 103 detects that the applicator 100 is no longer in contact with the body. This stopping of stimulation may be under the control of the control module to which the signal issued by the sensor 103 is returned, or indeed it may be stopped internally by the applicator itself, with the microprocessor installed therein being suitable for processing the data issued by the sensor 103 and for stopping stimulation.

Figure 2:
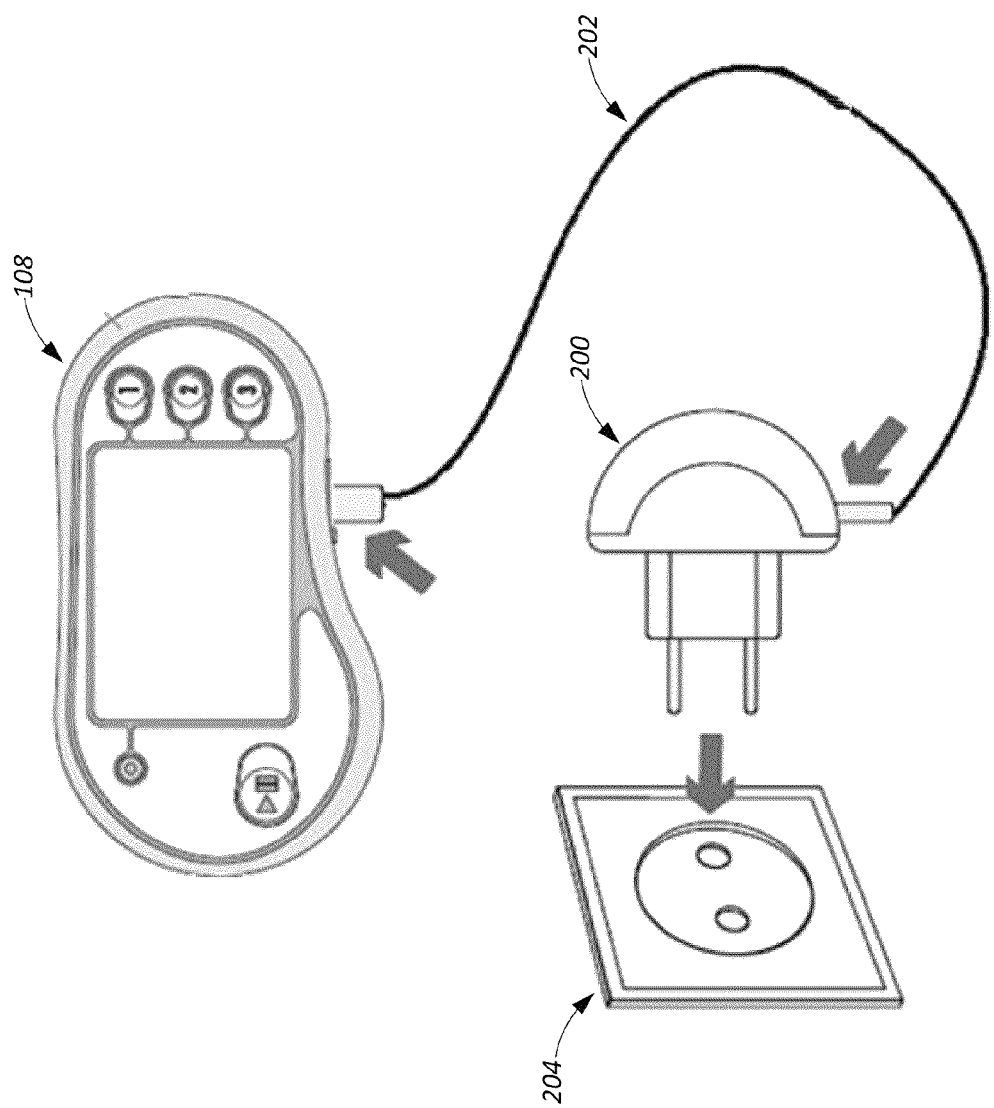
FIG. 2 shows an illustration of a perineal rehabilitation device during a charging stage, in accordance with some embodiments.

Reference is now made to FIG. 2, which shows an illustration of the device charging. Control module 108 may be connected to a charger 200 using a charging cable 202, which may be a USB cable. Charger 200 in turn, may be connected to a mains outlet 204, to allow charging.

Figure 3:
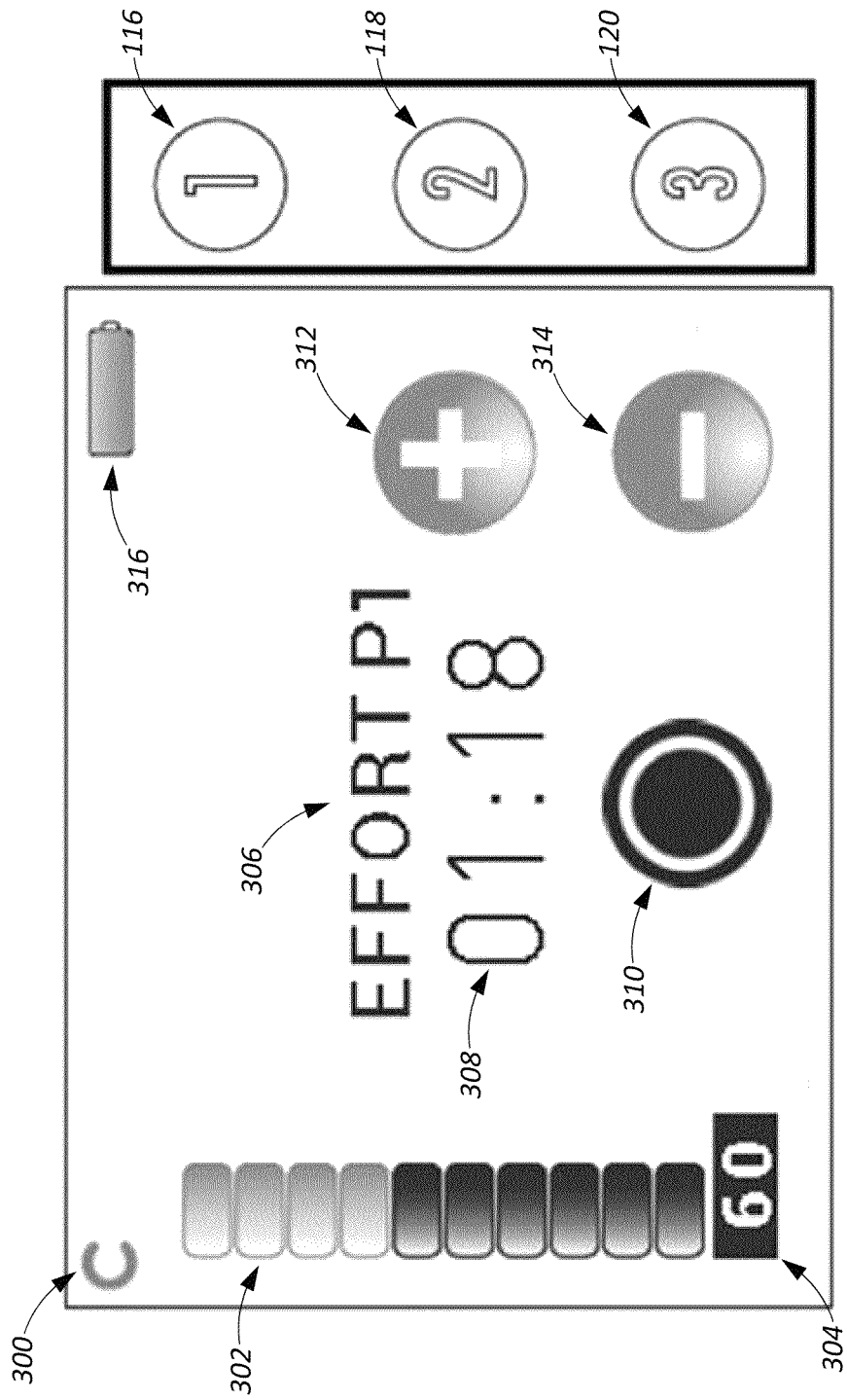
FIG. 3 shows an example of a display on the screen of the control module, in accordance with some embodiments.

Reference is now made to FIG. 3, which shows an example of a display on the screen of the control module. An indicator 300 may indicate whether connection with applicator 100 may be established or not (e.g. green indicator for communication and red indicator for no communication). An indicator 302 may indicate the stimulation intensity level graphically. An indicator 304 may indicate the stimulation intensity level numerically. An indicator 306 may specify the stimulation program (in this example "EFFORT P1") that may be running or may have been selected. An indicator 308 may display a timer showing the elapsed or remaining duration of the treatment. An indicator 310 may indicate that stimulation is currently operating. In this example, it may be depicted by a circle with a disk at its center that is lighted only when stimulation is active. Indicators 312 and 314 may indicate that multi-functional buttons 118 and 120 are now configured to increase or decrease stimulation intensity level, respectively. An indicator 316 may indicate the device battery level.

Figure 4:
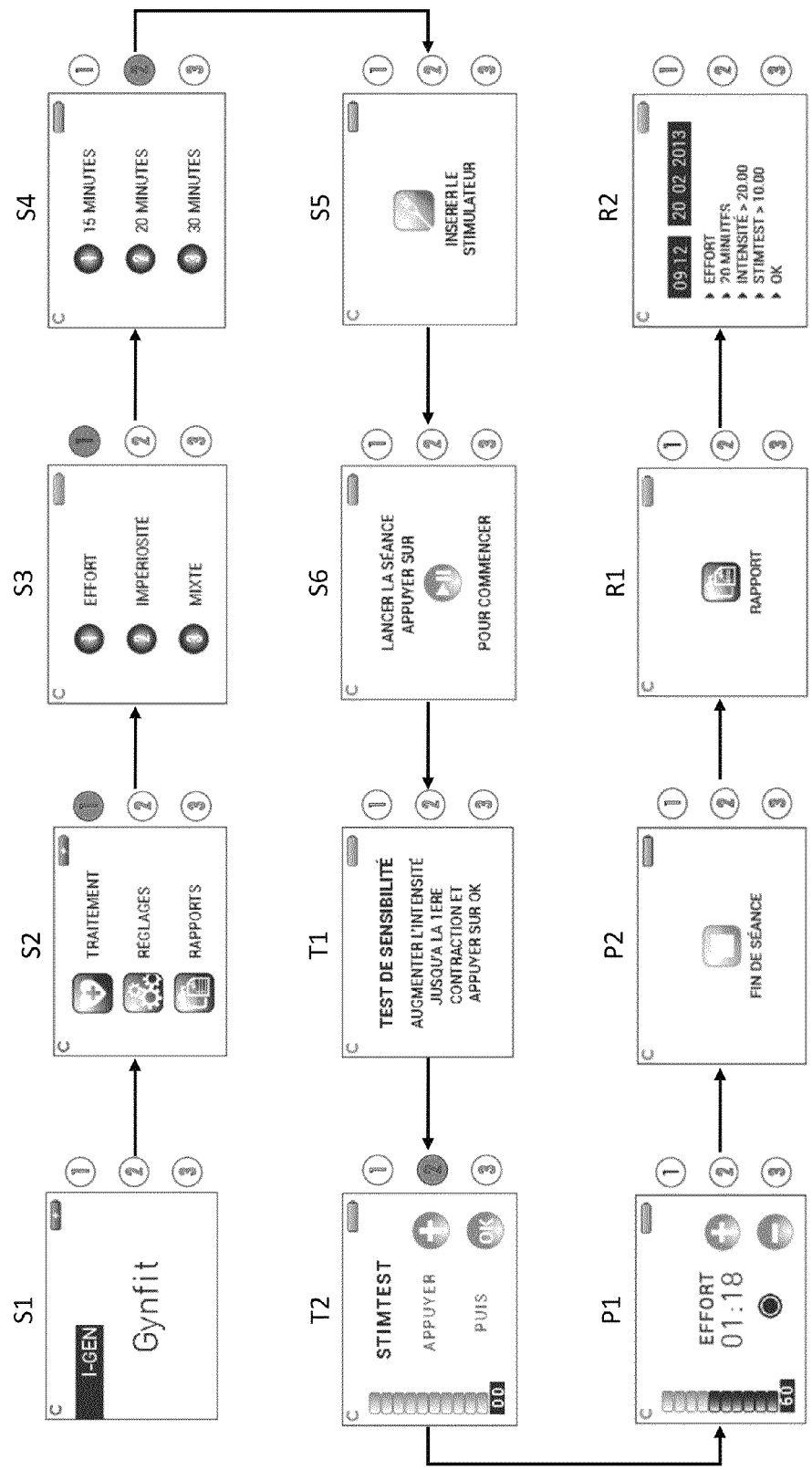
FIG. 4 shows a flow chart of the system operation, in accordance with some embodiments.

Reference is now made to FIG. 4, which shows a flow chart of the system operation. Control module 108 may be switched on using button 112, and screen 110 may display a "wake-up" indication, in step S1. Screen 110 may then invite the user to press on button 116 (herein button 1) in order to select a treatment option, in step S2. The user may be invited to select treatment program from a list of programs, using buttons 116, 118, and 120 (herein buttons 1, 2, and 3), in step S3. Specifically, the user may select from the following programs: Programs P1 and P2 may be dedicated for treating stress incontinence, and program P3 may be dedicated for treating mixed incontinence. The programs specific parameters may be given by the following table:

| Program | Frequency [Hz] | Pulse duration [μsec] | Stimulation time [sec] | Rest time [sec] | Recommended use |
|---------|----------------|-----------------------|------------------------|-----------------|------------------|
| P1 | 50 | 400 | 3 | 6 | 30 min, 3-5 times/week |
| P2 | 50 | 400 | 5 | 10 | 30 min, 3-5 times/week |
| P3 | 20 | 400 | 3 | 6 | 30 min, 3-5 times/week |

Afterwards, the system may invite the user to select the duration of the treatment, using buttons 116, 118, and 120 (herein buttons 1, 2, and 3), in step S4. The system may then invite the user to insert applicator 100 into the vagina, in step S5. The sensor 103 then serves to verify that the applicator 100 is indeed inserted before beginning the treatment. Advantageously, the signal issued by the sensor 103 is sent to the control module. The screen can then indicate whether or not the applicator 100 has been inserted correctly, and when the applicator is inserted correctly, the screen invites the user to press on the key in order to start the stimulation program. After applicator 100 may have been inserted correctly, the system may invite the user to press on button 114 in order to start the stimulation program, in step S6. Screen 110 may then display a message announcing of stimulation test start, in step T1. In step T2, the test sequence may begin with stimulation at zero intensity level to ensure that the patient does not suffer any electric shock, and the user may be invited to increase stimulation intensity level by pressing on "+", using button 118 (herein button 2). When she might feel a convenient level of stimulation, she may press "OK" using button 120 (herein button 3). Alternatively, the intensity level may be adjusted automatically by control module 108, according to body feedback (e.g. muscle contraction) measured by a sensor embedded in applicator 100 and transmitted to control module 108. The test may be performed at the beginning of each session, and allow obtaining important medical data, namely the user's sensitivity threshold and advancement level. A health professional may then measure the effectiveness of the treatment, knowing such data. The selected stimulation program may then put into operation in step P1. A timer counting down may appear and the user may increase and/or decrease the intensity level, using buttons 118 and 120 (herein buttons 2 and 3). Alternatively, the intensity level may be adjusted automatically by control module 108, according to body feedback (e.g. muscle contraction) measured by a sensor embedded in applicator 100 and transmitted to control module 108. While the program is running, indicator 310 may light up when a stimulation starts and may turn off when it stops. This may enable the user to know when stimulation is taking place in order to contract her muscles at the same time. In application of Kegel exercises, such contraction may encourage treatment and restoration or reinforcement of muscular structures. The user may also pause and/or resume the program momentarily, using 5 button 114. The duration of stimulation and its intensity may be stored automatically in the memory of control module 108. After the treatment session has finished, screen 110 may display an "end of session" indication, in step P2. Executed treatment session parameters may be automatically stored in control module memory. Thus, after session ending, screen 110 may automatically display a "report" indication, in step R1, immediately followed by a summary report of the executed treatment, in step R2. The report may include treatment session time and date, selected program, duration, average intensity level, stimulation test value, status of the session (completed successfully or not), etc. Treatment session history for all executed treatment sessions may be available to the user and/or health professional, by selecting the "Reports" option with button 120 (herein button 3), in step S2.

Figure 5:
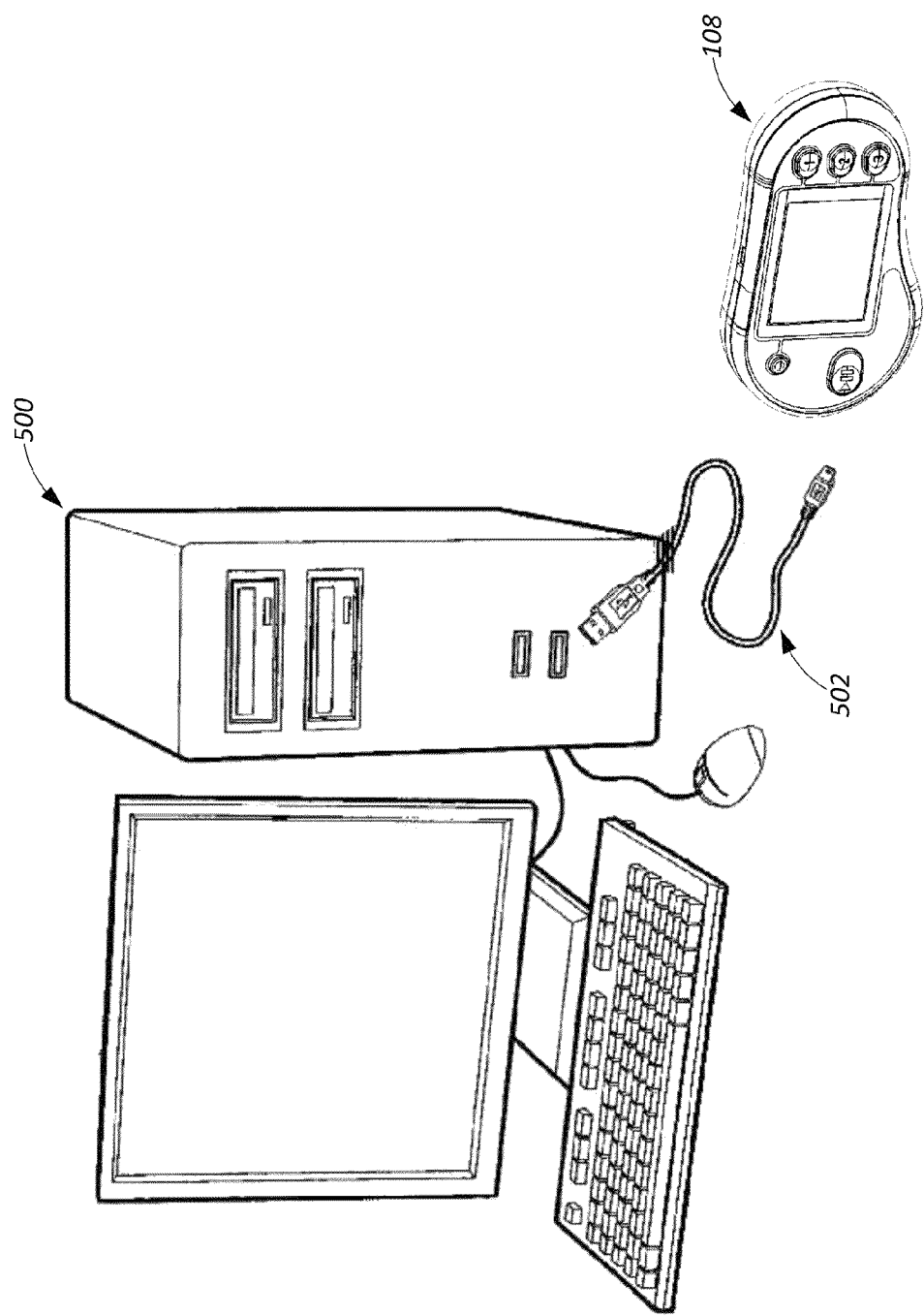
FIG. 5 shows an illustration of the optional connection of the control module to a computer, in accordance with some embodiments.

Reference is now made to FIG. 5, which shows an illustration of the optional connection of the control module to a computer. The connection between control module 108 and a computer 500 (e.g. the computer of the user or of a health professional) may be done by a USB cable 502. The data stored in memory of control module 108 may then be accessible by computer 500. It may also be possible to transfer the stored data to computer 500. Under such circumstances, the data may be subsequently presented using a format that may be suitable for reading that data by common software (e.g. Excel). In the context of biofeedback applications, it is advantageous also to store a so called "fitness" test showing the automatic adaptation of the intensity of stimulation as a function of progress during the application of the treatment. This may provide information about the fatigability of the muscle and about its training.

Figure 6A:
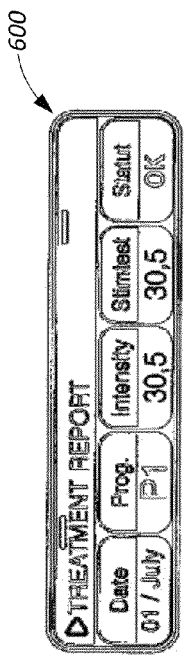
FIGS. 6A, B, and C show examples of data stored in the control module displayed on a computer screen, in accordance with some embodiments.
Figure 6B:
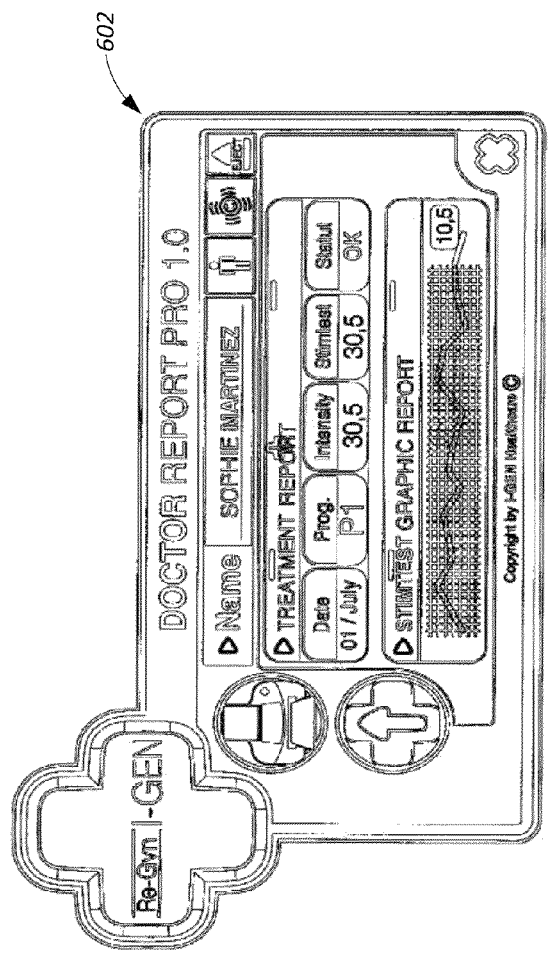
Figure 6C:
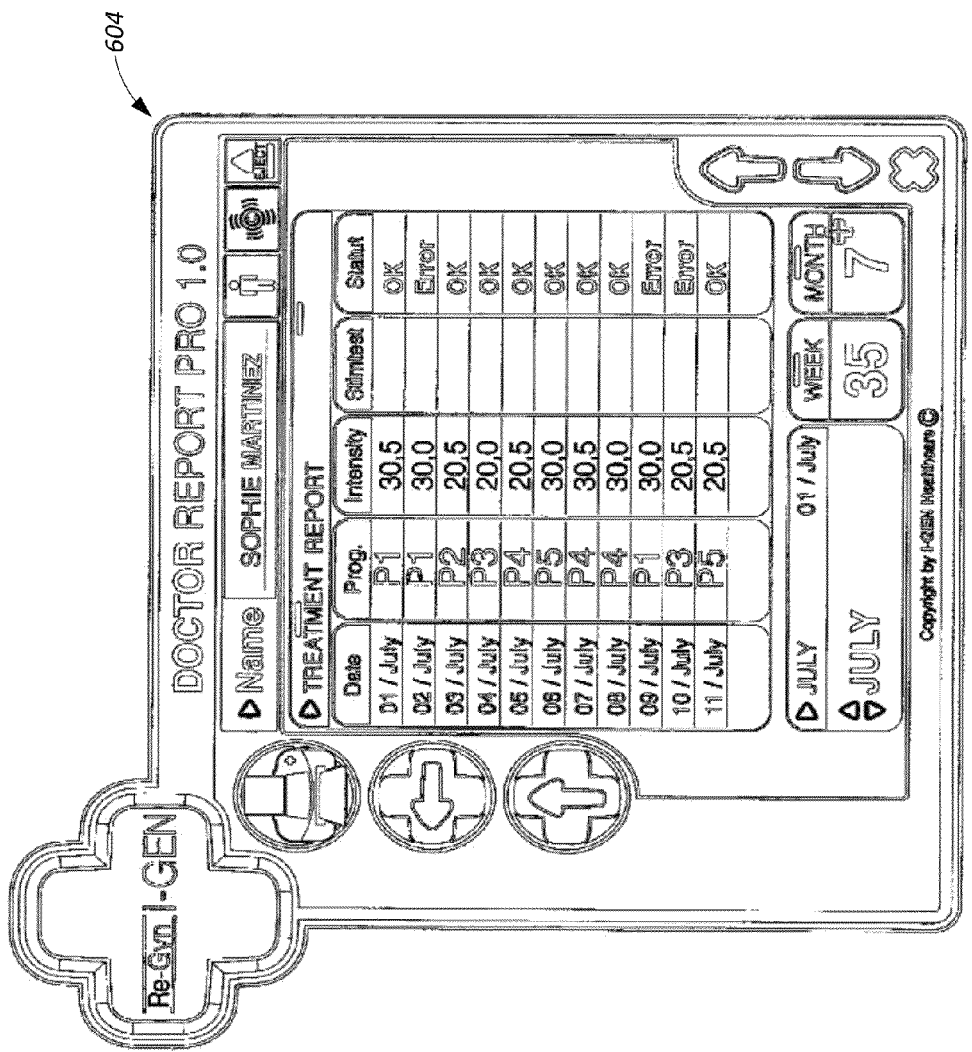

Reference is now made to FIG. 6, which shows an example of data stored in the control module displayed on a computer screen. FIG. 6A shows a compact window 600 which may include a summary report of a specific session, and detailed window 602 which may include additional data regarding that session (e.g. user name, graphical stimulation test summary, etc.). FIG. 6B shows a detailed window 604 which may include a list of treatment sessions performed by the user. The summary of the sensitivity tests in window 602 may be in the form of a curve of sensitivity threshold intensities detected by the user over the set of treatment sessions listed in window 604.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

What is claimed is:

1. A vaginal rehabilitative device comprising:
    a liquid-sealed vaginal electrical stimulation applicator, comprising:
        a) two stimulation electrodes configured to apply a voltage for executing an electrical stimuli, and
        b) a detection electrode that is configured to detect insertion of the applicator into a bodily cavity; and
    a control module connectable by a wire to said applicator and comprising (a) a user interface for controlling the electrical stimuli applied by said applicator and (b) a display module configured to display data received from said applicator,
    wherein, responsive to a signal from the detection electrode indicating that the applicator is inserted within the bodily cavity, the control module is configured to allow selection of a treatment program in accordance with a physiological sensitivity threshold determined via a sensitivity test, and
    wherein, responsive to a signal from the detection electrode indicating that the applicator is not inserted within the bodily cavity, the control module is configured to prevent the application of the electrical stimuli.

2. The device according to claim 1, wherein said applicator is shaped as an oblong cylinder.

3. The device according to claim 1, wherein said applicator further comprises a sensor configured (a) to detect muscular contraction in reaction to the electrical stimuli and (b) to adapt the electrical stimuli, in real time, corresponding to the muscular contraction.

4. The device according to claim 3, wherein said sensor is a pressure sensor configured to sense muscle contraction.

5. The device according to claim 1, wherein said applicator further comprises a sensor configured to detect a body reaction to the electrical stimuli and to provide feedback of treatment effectiveness corresponding to the body reaction.

6. The device according to claim 5, wherein said sensor is a pressure sensor configured to sense muscle contraction.

7. The device according to claim 1, wherein said control module further comprises at least one energy storage unit.

8. The device according to claim 1, wherein said control module further comprises at least one microprocessor.

9. The device according to claim 1, wherein said control module further comprises a memory configured for storing treatment history data.

10. The device according to claim 1, wherein said applicator and said control module are configured to communicate via a bidirectional wired communication protocol.

11. The device according to claim 1, wherein said control module is further configured to communicate with a computer via a wired communication protocol.

12. The device according to claim 1, wherein said control module is further configured to communicate with a computer via a wireless communication protocol.

13. The device according to claim 1, wherein each of the at least two stimulation electrodes is annular.

14. The device according to claim 13, wherein the at least two stimulation electrodes are disposed within the distal four centimeters of the applicator.

15. The device according to claim 1, wherein:
    responsive to a signal from the detection electrode indicating that the applicator is inserted within the bodily cavity, said control module is configured to perform the sensitivity test by:
        a) gradually increasing the intensity of the electrical stimuli;
        b) responsive to a signal received from said user interface indicating a moment at which the electrical stimuli begins to be felt by a user, defining the physiological sensitivity threshold in accordance with the indicated moment; and
        c) storing data corresponding to the physiological sensitivity threshold, thereby allowing the selection of the treatment program in accordance with the defined physiological sensitivity threshold.

\* \* \* \* \*